United States Patent
Herrema et al.

(10) Patent No.: US 7,745,197 B1
(45) Date of Patent: Jun. 29, 2010

(54) PROCESS FOR THE UTILIZATION OF RUMINANT ANIMAL METHANE EMISSIONS

(75) Inventors: Markus Herrema, Laguna Niguel, CA (US); Kenton Kimmel, Dana Point, CA (US)

(73) Assignee: Newlight Technologies, LLC, Costa Mesa, CA (US)

( * ) Notice: Subject to any disclaimer, the term of this patent is extended or adjusted under 35 U.S.C. 154(b) by 0 days.

(21) Appl. No.: 11/208,808

(22) Filed: Aug. 22, 2005

Related U.S. Application Data

(63) Continuation-in-part of application No. 10/687,272, filed on Oct. 15, 2003, now Pat. No. 6,982,161.

(60) Provisional application No. 60/603,857, filed on Aug. 24, 2004.

(51) Int. Cl.
  *C12N 1/30* (2006.01)
  *C12M 1/00* (2006.01)

(52) U.S. Cl. ............... 435/250; 435/289.1; 435/252.1; 435/254.1; 424/93.4; 424/93.5

(58) Field of Classification Search ............... 435/250, 435/289.1, 252.1, 254.1; 424/93.4, 93.5
See application file for complete search history.

(56) References Cited

U.S. PATENT DOCUMENTS

| | | | |
|---|---|---|---|
| 3,878,305 A * | 4/1975 | Damico et al. ............. | 426/104 |
| 4,375,515 A | 3/1983 | Patel et al. | |
| 4,524,569 A | 6/1985 | Hanna | |
| 5,344,766 A * | 9/1994 | Ramachandran et al. ... | 435/71.2 |
| H1430 H | 4/1995 | Apel et al. | |
| 5,434,062 A | 7/1995 | Groleau et al. | |
| 5,480,794 A | 1/1996 | Peoples et al. | |
| 5,642,630 A | 7/1997 | Abdelmalek et al. | |
| 5,727,903 A | 3/1998 | Borray et al. | |
| 5,747,584 A | 5/1998 | Noda | |
| 5,789,536 A | 8/1998 | Liggat et al. | |
| 5,842,357 A | 12/1998 | Siwajek et al. | |
| 5,849,894 A | 12/1998 | Clemente et al. | |
| 5,871,980 A | 2/1999 | Naylor et al. | |
| 5,894,062 A | 4/1999 | Liddell | |
| 5,942,597 A | 8/1999 | Noda et al. | |
| 6,043,063 A | 3/2000 | Kurdikar et al. | |

(Continued)

FOREIGN PATENT DOCUMENTS

WO WO2007/024255 3/2007

(Continued)

OTHER PUBLICATIONS

Johnson et al., "Methane emissions from cattle," J Anim Sci 73:2483-2492, 1995.*

(Continued)

*Primary Examiner*—Karen Cochrane Carlson
*Assistant Examiner*—Rosanne Kosson
(74) *Attorney, Agent, or Firm*—Knobbe, Martens, Olson & Bear, LLP

(57) ABSTRACT

A process for the utilization of the methane produced by enteric fermentation, specifically to a process that utilizes methane produced by ruminant animals through enteric fermentation as a source of carbon and/or energy for the directed production of methane-based goods or processes is provided.

7 Claims, 6 Drawing Sheets

U.S. PATENT DOCUMENTS

| | | | |
|---|---|---|---|
| 6,051,411 | A | 4/2000 | Turtakovsky et al. |
| 6,205,704 | B1 | 3/2001 | Schmitz et al. |
| 6,395,520 | B1 | 5/2002 | Babel et al. |
| 6,446,385 | B1 | 9/2002 | Crutcher |
| 6,599,423 | B2 | 7/2003 | Boles et al. |
| 6,666,027 | B1 | 12/2003 | Cardenas, Jr. |
| 6,709,849 | B2 | 3/2004 | Cheung |
| 6,749,368 | B2 | 6/2004 | Ankeny et al. |
| 6,770,464 | B2 | 8/2004 | Steinbuchel et al. |
| 6,982,161 | B1 | 1/2006 | Herrema |
| 7,098,298 | B2 | 8/2006 | Kinoshita et al. |
| 7,141,400 | B2 | 11/2006 | Yu |
| 7,455,999 | B2 | 11/2008 | Madison et al. |
| 2008/0160569 | A1 | 7/2008 | Ho et al. |
| 2008/0241886 | A1 | 10/2008 | Merrema et al. |

FOREIGN PATENT DOCUMENTS

| | | |
|---|---|---|
| WO | WO2008/103134 | 8/2008 |

OTHER PUBLICATIONS

Cow Power, http://www.riverdeep.net/current/2002/03/032502t_cowpower.jhtml, Mar. 2002.*

Gasser, "Agricultural productivity and the nitrogen cycle," Phil Trans R Soc Lond B296;303-314, 1982.*

Gay, S.W., "Natural ventilation for freestall dairy barns," Pub. No. 442-763, Virginia Cooperative Extension, Virginia Polytechnic Institute and State University, http://www.ext.vt.edu/pubs/bse/442-763/442-763.pdf, 2002.*

Climate Change 2001: Working Group I: The Scientific Basis, Intergovernmental Panel on Climate Change, http://www.grida.no/climate/ipcc_tar/wg1/017.htm, 2001.*

Polakovic, "Getting the Cows to Cool It," Los Angeles Times, Jun. 7, 2003, pp. A1-A17, Los Angeles, CA U.S.A.

Bartle, "Exploiting a Gascating Bacteria," University of Bergen Magazin, 2002, at http://www.uib.no/elin/elpub/uibmag/en02/bacteria.html.

D'Aquino, "Methane to Protein," at http://www.aptagen.com/corporate/AptagenDocuments/Articles/che.html., Oct. 2000.

Wendlandt et al., "Producing poly-3-hydroxybutyrate with a high molecular mass from methane," J. Biotechnol. 2001, vol. 86, pp. 127-133, see pp. 127-128.

Co-Pending U.S. Appl. No. 11/676,928, filed Feb. 20, 2007. Title: Method for the Production of Polyhydroxyalkanoic Acid. Inventors: Herrema et al.

Meeting Minutes of Methane to Markets, Agriculture Task Force Meeting dated Jun. 22, 2005. http://www.methanetomarkets.org/resources/ag/docs/ag-meeting.pdf.

Methane Emissions from Livestock Enteric Fermentation (p. 150). Reducing Emissions of Non-CO2 Greenhouse Gases (Sep. 2006). http://www.climatetechnology.gov/stratplan/final/CCTP-StratPlan-Ch07-Sep-2006.pdf.

3. How can livestock methane emissions be reduced? Ruminant Livestock (Mar. 2007). http://www.epa.gov/methane/rlep/faq.html.

The abatement challenge for Australian Agriculture (2007). Enteric methane (p. 2). http://www.dpc.vic.gov.au/CA256D800027B102/Lookup/Forum1EckardPaper/$file/Eckard%2017%20August%202007%20-%20The%20abatement%20challenge%20for%20agriculture.pdf.

5—Potential management practices and technologies for reducing methane emissions from agriculture. http://www.maf.govt.nz/mafnet/rural-nz/sustainable-resource-use/climate/green-house-gas-migration/ghg-mitigation-05.htm, accessed Apr. 16, 2008.

Technologies for Reducing Non-Energy-Related Emissions (Mar. 2006). Enteric Fermentation (p. 8). http://www.cfses.com/documents/climate/10_%20Jolley_Technologies_for_Reducing_Non-energy_Related_Emissions.pdf.

Matter 2.0 (Jul. 1999). 5.1.1 Enteric fermentation (p. 22). ftp://ftp.ecn.nl/pub/www/library/report/1999/c99048.pdf.

Johnson, K.A. and Johnson D.E. "Methane emissions from cattle". J. Anim Sci 1995. 73:2483-2492.

Nichols, Peter D., and White, D.C., "Accumulation of poly-B-hydroxybutyrate in a methane-enriched, halogenated hydrocarbon-degrading soil column: implications for microbial community structure and nutritional status". Hydrobiologia 1989, 176/177:369-377.

International Search Report and Written Opinion of PCT Application No. PCT/US05/47415.

International Preliminary Report on Patentability of PCT Application No. PCT/US05/47415.

Gooch, Curt A., *Natural or Tunnel Ventilation of Freestall Structures: What is Right for Your Dairy Facility?* www.milkproduct.com, Published Nov. 4, 2005.

Tyson, John T. et al., Tunnel Ventilation for Tie Stall Dairy Barns, *Penn State, College of Agricultural Sciences, Agricultural and Biological Engineering*, $2^{nd}$ Edition Jan. 1, 2004.

Bioremediation—field Experience: Field Experience, Paul E. Flathman, Douglas E. Jerger and Jurgen H. Exner, CRC Press, Boca Raton, Florida, 1994, pp. 275-276.

Brigmon, Methanotrophic Bacteria: Use in Bioremediation, Westinghouse Savannah River Company, on-line publication No. WSRC-MS-2001-00058, http://sti.srs.gov/fulltext/ms2001058/ms2001058.html,2001.

Murrell et al., "Regulation of expression of methane monooxygenases by copper ions,"Trends in Microbiology 8(5):221-225, 2000.

Frans-Jaco, et al., "Spatial Distribution and Inhibition by Ammonium of Methane Oxidation in Intertidal Freshwater Marshes" Applied and Environmental Microbiology, (1997) vol. 63(12): 4734-4740.

Jensen, S. et al., "Methanol Improves Methane Uptake in Starved Methanotrophic Microorganisms" Applied and Environmental Microbiology, (1998) vol. 64(3): 1143-1146.

McDonald et al., "The Soluble Methane Monooxygenase Gene Cluster of the Trichloroethylene-Degrading Methanotroph *Methylocystis* sp. Strain M," Applied and Environmental Microbiology, 1997, vol. 63, pp. 1898-1904.

Norferm's future under discussion; Scandinavian Oil-Gas Magazine; http://www.scandoil.com/moxie-bm2/news/company_news/norferms-future-under-dis.shtml, Published Oct. 27, 2005.

Wendlandt et al., "Possibilities for controlling a PHB accumulation process using various analytical methods," J. of Biotechn. 2005, vol. 117, pp. 119-129.

\* cited by examiner

PROCESS FOR THE UTILIZATION OF RUMINANT ANIMAL METHANE EMISSIONS

RELATED APPLICATIONS

This application is a continuation-in-part of patent application Ser. No. 10/687,272, filed Oct. 15, 2003 now U.S. Pat. No. 6,982,161 and claims the benefit of Provisional Application No. 60/603,857, filed Aug. 24, 2004, all incorporated by reference herein.

BACKGROUND OF THE INVENTION

1. Field of Invention

This invention relates generally to processes for the reduction of ruminant animal methane emissions, specifically to a process for the utilization of ruminant animal methane emissions as a source of energy.

2. Description of the Related Art

Methane emissions from ruminant animals account for about twenty percent of total global methane emissions, and atmospheric methane accounts for about twenty percent of planetary warming. In addition to the environmentally destructive effects of ruminant animal methane emissions, such emissions represent wasted energy, as a significant percentage of the food ruminant animals eat is lost as methane. Accordingly, there have been significant efforts in the past to reduce ruminant animal methane emissions.

Ruminant animal methane emissions, or, more specifically, enteric fermentation methane emissions, originate in the four-stomach digestive tract common to all ruminant animals, which includes the rumen, a large forestomach connected to the four-stomach digestive tract. The rumen contains a host of digestive enzymes, fungi, bacterium, and protozoa, and the bulk of digestion, as well as methane production via enteric fermentation, takes place here. Not surprisingly, all prior efforts to reduce enteric fermentation methane emissions from ruminant animals, which include dairy cows, beef cattle, sheep, goats, water buffalo, and camels, have focused on modifications associated with the rumen or digestive tract.

Past modification efforts have included: vaccines designed to limit methanogenic, or methane-producing, microorganisms in the rumen or digestive tract; feed reformulations designed to alter the chemical or microbial environment of the rumen or digestive tract to limit methane production; feed reformulations designed to decrease the amount of methane-producing foods entering the rumen or digestive tract; and selective breeding aimed at encouraging the reproductive success of ruminant animals which produce relatively low amounts of methane, presumably as a result of factors associated with the rumen or digestive tract.

While most of these prior efforts have had some success in reducing enteric fermentation emissions, none has been shown to completely, or even significantly, eliminate ruminant animal methane production. Since limited success in reducing methane production concurrently limits the economic benefits of using methane-reducing vaccines, feed formulations, or selective breeding, ruminant animal owners have generally been averse or reluctant to employ these methods. Thus, as the ruminant animal population continues to grow in accord with ever-increasing worldwide demand and methane reduction efforts fail to reduce emissions in any significant way, enteric fermentation methane emissions remain a significant source of both environmental degradation and wasted energy.

Prior to the applicants' discovery, no methods were known to reduce ruminant animal methane emissions by using such methane as a source of energy in energy consumption systems maintained outside of the digestive tracts of ruminant animals. In the past, all ruminant animal methane reduction processes have focused on limiting ruminant animal methane production rather than reducing overall atmospheric emissions through a system of methane utilization. Thus, it is one feature of several embodiments of the present invention that ruminant methane emissions are reduced through the utilization of ruminant animal methane as a source of energy.

Methane-utilizing, or methanotrophic, microorganisms are well known in the microbiology art for their capacity to grow and reproduce using methane as a source of carbon and/or energy. Methanotrophic microorganisms, specifically bacteria, have even been employed to reduce ruminant animal methane emissions by being placed directly in the rumen or digestive tract of ruminant animals and subsequently limiting production at its source. They have never, though, been employed in a microbiological growth system. They have also never been employed in a microbiological growth and harvest system that reduces ruminant animal enteric fermentation methane emissions while concurrently providing a means for harvesting products of microorganism growth, such as microorganism biomass. Methods for the utilization or consumption of methane gas as a source of feedstock fuel, including fuel used for the production heat, electricity, liquid natural gas, compressed natural gas, chemicals, industrial feedstock, and a range of other goods, are well known for their capacity to use methane as a source of energy. However, none of these methods has ever been employed to reduce enteric fermentation methane by using such methane as a source of energy for the induction of methane-based processes or for the production of electricity, heat, and/or other methane-based products.

Prior to the applicants' discovery, no methods were known to utilize ruminant animal methane emissions as a source of energy. More specifically, the connection between enteric fermentation methane emissions from ruminant animals and the directed production of methane-based goods or methane-driven processes through the utilization of enteric fermentation methane as a source of carbon and/or energy had ever been made. At least two major factors likely inhibited such a connection. First, it is not a well-known fact that, under certain conditions, certain ruminant animals produce enough methane to make methane-consumption systems such as electricity, heat, or microorganism production platforms technically and/or economically feasible. Second, ruminant animal methane emissions are not considered a viable source of carbon or energy because they are considered low-volume, non-concentrated, and, thus, unusable methane emissions. While up to ninety-five percent of enteric fermentation methane emissions exit the digestive tracts of ruminant animals as exhalation, most continue to regard such emissions as components of low-volume, diffuse, unusable flatulence. No methods are known to capture and/or consolidate enteric fermentation methane emissions in a way that would convert them into a state suitable for use as a fuel stream for the production of methane-based goods or processes. Enteric fermentation methane originates as diffuse emissions, and no methods are known to convert such emissions into a usable form. For these and other reasons, ruminant animal methane emissions have never been considered as a viable source energy, and the connection between enteric fermentation methane emissions and methane-driven process and goods production has never occurred.

Mechanical ventilation systems are well known in the livestock and agricultural science art for their capacity to draw, push, or pull air through a fully or partially enclosed ruminant animal holding, feeding, or enclosure area. The main function of mechanical ventilation systems, including tunnel ventilation systems and other ventilation systems, is to provide air flow or air exchange in order to maintain or improve the health of ruminant animals in a fully or partially enclosed holding or feeding area. It is also well known in the livestock and agricultural science art that some mechanical ventilation systems, particularly tunnel ventilation systems, have the capacity to force all or some of the air inside a fully or partially enclosed ruminant animal holding or feeding area through specific vents or fans. The outflow air coming out of ventilation fans have even been forced, directed, or led into mulch, compost, and/or other platforms designed to limit or reduce outflow air odor or dust emissions. Prior to the applicants' discovery, though, such ventilation systems used in conjunction with enclosure structures had never been considered as means to enable the capture, consolidation, and utilization of ruminant animal methane emissions as a source of energy. It is one feature of several embodiments of the present invention that animal enclosure structures and/or ventilation systems are applied as means to capture, consolidate, direct, and/or convey ruminant animal methane emissions to enable the use of such emissions as a source of energy. Prior to the applicants' discovery, ventilation systems and/or enclosure structures had never been used to capture ruminant animal enteric fermentation methane emissions, nor had such emissions ever been used to grow bacteria in a bioreactor optionally equipped with means to harvest any of the microbial products associated with bioreactor activity, particularly microbial biomass. Similarly, prior to the applicants' discovery, ventilation systems and/or enclosure structures had never been used to capture enteric fermentation methane for utilization by a methane-consumption system such as a reverse-flow reactor or microturbine. The utilization of air conveyance systems to capture enteric fermentation methane for use as a source of carbon and/or energy overcomes a range of practical problems associated with a system for capturing methane emissions from the nose and/or mouth of a ruminant animal using on-animal apparatuses such as bioreactors or microturbines, including animal mobility problems and reactor size requirements for optimal methane conversion. The straightforward utilization of structures, means, and systems that are well known and/or commonly used also overcomes a range of prior emissions capture problems, including practicability, palatability, and viability. One of skill in the art will understand that currently available and other ventilation systems can be used in accordance with embodiments of the invention.

No previous methods were known to reduce ruminant animal methane emissions by using such methane as a source of energy. Consequently, ruminant animal methane emissions remain a significant source of environmental degradation.

Several embodiments of the present invention relate to a process for the utilization of the methane produced by ruminant animals through enteric fermentation as a novel source of energy.

Embodiments of the invention have several surprising and unexpected advantages over the prior art, some of which are surprising and unexpected. One or more of these advantages are present in certain preferred embodiments of the present invention. Further objects and advantages will become apparent from the ensuing description.

SUMMARY OF THE INVENTION

In accordance with several embodiments of the invention, a process wherein the methane produced through ruminant animal enteric fermentation is utilized as a source of carbon and/or energy for the induction of a methane-driven process and/or for the production of methane-derived materials, such as methane-utilizing microorganisms, heat, and/or electricity. In one embodiment of a process carried out in accordance with the invention, this process may be accomplished by a) enclosing one or more ruminant animals in an enclosure means, such as a barn, and b) contacting air contained in such an enclosure means, including the enteric fermentation methane contained therein, with a methane-consumption system, whereby enteric fermentation methane emissions are utilized as a novel source of carbon and/or energy for the induction of a methane-based process and/or for the production of methane-based products, such as heat, electricity, and/or methane-utilizing microorganisms.

In another embodiment, a method for producing methane-based products or processes in a confined apparatus comprising using the enteric fermentation methane produced by one or more ruminant animals as a source of carbon and/or energy for the production of methane-based products or processes is provided. In one embodiment, this method comprises: (a) providing one or more ruminant animals, (b) providing enteric fermentation-derived methane gas that has been emitted by the animals, including air containing the methane, (c) providing means to capture, consolidate, and/or direct the methane, including providing an enclosure means to enclose the animals, the air, and the methane and providing an air conveyor means to direct the air and the methane, (d) providing a methane-consumption means which can use the methane as a source of carbon and/or energy in a methane-based process and/or for the production of methane-based goods, and (e) contacting the methane with the methane-consumption means to cause the methane-consumption means to oxidize, consume, and/or otherwise utilize the methane for the operation of a methane-based process or for the production of one or more methane-based products, including methane-utilizing microorganisms, heat, and/or electricity.

In another embodiment, this method comprises: (a) providing one or more ruminant animals, (b) providing an enclosure means to fully or partially enclose and/or otherwise encapsulate the animals, (c) providing enteric fermentation-derived methane gas that has been emitted by the animals, (d) providing enclosure air that has been combined with the methane in the enclosure means, (e) providing a methane-consumption means which can use the methane as a source of carbon and/or energy for the induction of a methane-based process or the production of methane-based goods, (f) providing a means for contacting the air containing the methane with the methane-consumption means, including a means for the conveying the air to the methane-consumption means whereby the methane can be utilized as a source of carbon and/or energy by the methane-consumption means, (g) mutually-contacting and/or exposing the methane and the methane-consumption means to cause the methane-consumption means to oxidize, consume, and/or otherwise utilize the methane for the induction of one or more methane-based processes or for the production of one or more methane-based products, including methane-utilizing microorganisms, heat, and/or electricity, whereby the methane produced by the animals is utilized for the sustained production of the process and/or the products in a specified apparatus.

As discussed previously, methane is an environmentally-destructive material and previously unusable source of energy, which, according to one preferred embodiment of the invention, is used to produce a useful end-product that can be used or sold for use, providing an economic incentive to a ruminant animal methane emissions reduction effort. In one embodiment, the end-product is heat. In another embodiment, the end-product is fuel. In yet another embodiment, the end-product is electricity. In yet another embodiment, the end-product is another form of energy. In a further embodiment, the end-product is the culture of micro-organisms.

In one embodiment, the enclosure means includes any means by which the animals are fully or partially enclosed or encapsulated. The enclosure means includes, but is not limited to, a barn, greenhouse, and/or any other suitable enclosures or housing.

In one embodiment, the term "air" as used herein shall be given its ordinary meaning, and shall include all airborne and gaseous components of air that has been contacted with the methane in the enclosure means, including the methane emitted by the animals contained within the enclosure means, as well as ammonia gas, dust, and/or other airborne materials that may be present in the air.

In one embodiment, methane-consumption means includes any means by which the methane is oxidized, consumed, and/or otherwise used as a form of carbon and/or energy. Methane-consumption means includes, but is not limited to, methane-utilizing microorganisms, fuel cells, turbines, reverse-flow reactors, engines, microturbines, and/or any other methane-consumption means.

In one embodiment, the ammonia contained within the air is contacted with liquid water and converted into ammonium and used as a source of nitrogen by the methane-utilizing microorganisms.

In one embodiment, the dust and/or other airborne material within the enclosed air is reduced prior to or in the course of using the methane within the air as a source of carbon and/or energy.

In one embodiment, the methane within the air is used by the methane-consumption means in conjunction with alternative sources of methane, such as coal mine methane, landfill gas methane, natural gas methane, manure digester methane, wastewater treatment methane, and/or other sources of methane.

In one embodiment, a method for producing methane-based products or processes using the enteric fermentation methane produced by one or more ruminant animals as a source of carbon and/or energy, comprising: (a) providing one or more ruminant animals, (b) providing enteric fermentation-derived methane gas that has been emitted by said animals, (c) providing an enclosure to fully or partially enclose and/or otherwise encapsulate said animals, (d) providing enclosure air that has been combined with said methane in said enclosure, (e) providing a methane-consumer which can use said methane as a source of carbon and/or energy for the operation of a methane-based process and/or for the production of methane-based goods, (f) contacting said methane-consumer with said enclosure air containing said methane to cause said methane-consumer to oxidize, consume, and/or otherwise utilize said methane for the operation of a methane-based process or for the production of one or more methane-based products, including but not limited to methane-utilizing microorganisms, heat, and/or electricity.

In one embodiment, an air conveyor is provided to direct, move, and/or otherwise convey enclosure air, wherein can be used to contact said air with said methane-consumer.

In one embodiment, the methane-consumer is one or more of the following: methane-utilizing microorganisms, fuel cells, microturbines, turbines, methane-based engines, and/or reverse-flow reactors.

In one embodiment, the enclosure is erected, modified, and or used to enclose the animals and to make the methane available for use by the methane-consumer.

In one embodiment, the air comprises air, dust, methane, ammonia, gases, flies, particulate matter, and/or other airborne matter fully or partially contained by the enclosure.

In one embodiment, the methane and the methane-consumer are contacted for the purpose of reducing emissions of the methane and/or the dust, the ammonia, the particulate matter, and/or other components of the air.

In one embodiment, the methane is used to generate electricity and/or heat.

In one embodiment, the methane is contacted with the methane-consumer to reduce methane emissions and/or simultaneously create harvestable products.

In one embodiment, a method for producing methane-based products or processes using the enteric fermentation methane produced by one or more ruminant animals as a source of carbon and/or energy, comprising collecting air containing the methane and conveying the air to a methane-consumption system that will utilize the methane within the conveyed air for the production of one or more methane-based processes and/or products.

In one embodiment, the methane-consumption system is any system that can utilize the air as a feedstock fuel stream for the production of a methane-based process or product, wherein the system may be a methane-utilizing microorganism growth system, a microturbine system, a reverse-flow reactor system, and/or any other methane-driven system.

In one embodiment, the enclosure is provided and utilized to collect said air containing said methane.

In some embodiments, one of skill in the art will appreciate that one or more of the above steps described herein is modified or omitted. Further, the steps need not be conducted in the order set forth herein.

Besides the objects and advantages described herein, some advantages of several embodiments of the present invention include:

(a) to provide a process that converts previously harmful emissions in the form of the methane produced by ruminant animals through enteric fermentation into useful goods;

(b) to provide a process which overcomes previously insurmountable problems in the continuous collection and utilization of ruminant animal methane emissions;

(c) to provide a process which provides a direct economic incentive for ruminant animal methane emission reductions;

(d) to provide a process which reduces ruminant animal enteric fermentation methane emissions without altering the chemical or microbial make-up of the digestive tract of ruminant animals;

(e) to provide a process which reduces ruminant animal methane emissions without requiring ruminant animals to alter their normal/natural behavior patterns, including sleeping and nutrient-consumption;

(f) to provide a process which reduces ruminant animal methane emissions without requiring feed reformulations, selective breeding activities, or chemical or microbial modifications to the digestive systems of ruminant animals;

(g) to provide a process which can be integrated into ruminant animal ownership operations;

(h) to provide a process which improves living conditions for ruminant animals, (h) to provide a process which reduces dust, ammonia, and/or odor problems associated with ruminant animal operations, (i) to provide a process which reduces enteric fermentation methane emissions through a system of methane utilization, and/or (j) to provide a process which converts an environmentally destructive greenhouse gas into a harvestable and economically valuable end-product, such as microorganism biomass, heat, and/or electricity.

BRIEF DESCRIPTION OF THE DRAWINGS

FIG. 2A is a top cross-sectional view of one of two parts of the apparatus depicted in FIG. 1. The part of the apparatus illustrated is the permanent exhalation conveyance structure that is attached to the body of a ruminant animal.

FIG. 2B is a side perspective view of one of two parts of the apparatus depicted in FIG. 1. The part of the apparatus illustrated is the permanent exhalation conveyance structure that is attached to the body of a ruminant animal.

FIG. 3A is a side cross-sectional view of one of two parts of the apparatus depicted in FIG. 1. The part of the apparatus illustrated is the removable microorganism containment capsule that is inserted into the permanent exhalation conveyance structure.

FIG. 3B is a side perspective view of one of two parts of the apparatus depicted in FIG. 1. The part of the apparatus illustrated is the removable microorganism containment capsule that is inserted into the permanent exhalation conveyance structure.

DETAILED DESCRIPTION OF THE PREFERRED EMBODIMENTS

Figure 1:
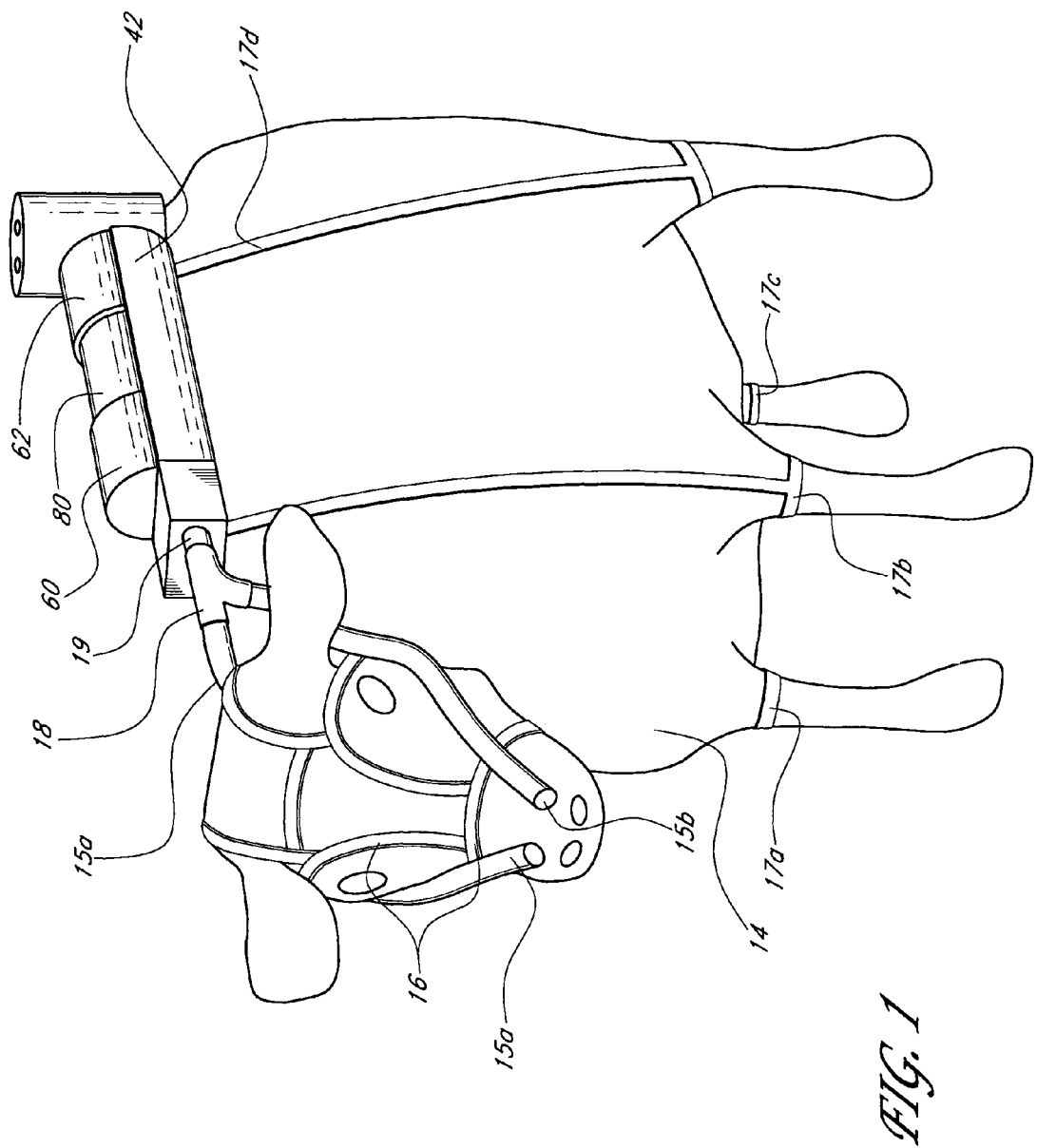
FIG. 1 is a side perspective view of an apparatus used to carry out a process in accordance with on embodiment of the invention. In the illustration, the apparatus is self-contained and maintained entirely on the body of a ruminant animal.

While this invention is susceptible to embodiments in many different forms, there is shown in the drawings and will herein be described in detail preferred methods of carrying out a process in accordance with embodiments of the invention with the understanding that the present disclosure is to be considered as an exemplification of the principles of the invention and is not intended to limit the broad aspect of the invention to the embodiment illustrated.

As used herein, the terms "ruminant animal methane", "enteric fermentation methane", and "ruminant animal enteric fermentation methane" shall be given their ordinary meaning and shall also refer to any methane produced and emitted by one or more ruminant animals as a result of processes associated with enteric fermentation. An average adult dairy cow will emit approximately 150 kg of enteric fermentation methane per year, while beef cattle will each produce about two-thirds of that volume, or 100 kg per year. Methane emitted by ruminant animals is a particularly important greenhouse gas, since on a ton-to-ton basis it has 21 to 23 times the heat-trapping capacity of carbon dioxide.

The term "consolidation means" shall be given its ordinary meaning and shall also refer to any means by which enclosure air is unified, mutually-directed, and/or otherwise consolidated for conveyance. In one preferred embodiment, a consolidation means comprises an air-tight ducting tube running from an air outlet to a mutual-exposure means, as described below, wherein enclosure air is directed out of an enclosed area, through a consolidation means, and into a mutual-exposure means. In another preferred embodiment, a consolidation means comprises multiple ducting tubes connected to air outlets and situated to consolidate outflowing enclosure air into a single ducting tube that ultimately leads as one or more air streams into a methane-consumption system.

The term "ventilation means" shall be given its ordinary meaning and shall also refer to any means by which air, gases, and/or other airborne material is mechanically forced, pushed, pulled, drawn, moved, conveyed, or otherwise directed into, through, and/or out of a spatial area enclosed by an enclosure means. In one preferred embodiment, well-known ventilation fans, such as rotating ventilation fans and/or tunnel ventilation fans, operate in a well-known barn ventilation process, whereby air may be drawn into a barn through one or more open spaces in a barn wall and directed out of a barn through ventilation fans. In one preferred embodiment, an enclosure means is provided with ventilation means, wherein air is moved into and out of an enclosure means at an overall combined rate of 10 cubic feet per minute per dairy cow. In one preferred embodiment, means for the cooling of barn-enclosed air are also provided in order to ensure animal well-being in an enclosed area. A number of air-cooling means are well known, such as cooling pads, water sprayers, and air conditioning units.

The term "ruminant animal" shall be given its ordinary meaning and shall also refer to one or more ruminant animals, including, as in one preferred embodiment, a dairy or beef cow.

The terms "enclosure means" and "means for enclosure" shall be given their ordinary meaning and shall also refer to any means by which some or all of the space in which one or more ruminant animals exist is partially or fully confined, isolated, encapsulated, and/or enclosed, such as a barn or greenhouse structure. In one preferred embodiment, a barn with a specified air inlet, such as a window, and a specified air outlet, such as a window housing a ventilation fan, encloses a ruminant animal (e.g., dairy cow).

The term "air inlet" shall be given its ordinary meaning and shall also refer to any location where air, gas, and/or other airborne material enters into an area or chamber fully or partially enclosed by an enclosure means. In one preferred embodiment, an air inlet comprises a spatial opening, such as a window, in the wall of an enclosure means.

The term "air outlet" shall be given its ordinary meaning and shall also refer to any location where air, gas, and/or other airborne material exits out an area or chamber fully or partially enclosed by an enclosure means. In one preferred embodiment, an air outlet comprises a spatial opening housing a ventilation means located in the wall of an enclosure means.

The term "enclosure air" shall be given its ordinary meaning and shall also refer to the air, gases, and/or other airborne material that have been mixed with enteric fermentation methane in the space fully or partially enclosed by an enclosure means, including enteric fermentation methane, ammonia, dust, and/or other airborne material contained within an enclosure means containing a ruminant animal.

Methane-utilizing microorganisms represent one embodiment of a "methane-consumption system" or "methane consumption means", that is, e.g., a mechanical, chemical, and/or biological system that utilizes enteric fermentation methane as a source of carbon and/or energy. The term "methane-utilizing microorganisms" shall be given its ordinary meaning and shall also refer to any microorganism, naturally-occurring or genetically-engineered, that utilizes methane, including enteric fermentation methane, as a source of carbon and/or energy. The term "methane-utilizing microorganisms" also refers to the mixture of methane-utilizing and non-methane-utilizing microorganisms that are collectively associated with the growth of methane-utilizing microorganisms. In one embodiment, this microorganisms mixture includes one or more of the following: *Methylococcus capsulatus, Alcaligenes acidovorans, Bacillus firmus*, and *Bacillus brevis*. In one embodiment, a mixture of these microorganisms is used because among other advantages this mixture is known to promote the long-term growth of *Methylococcus* capsulatus. The term "methane-utilizing microorganisms" also includes any methanotrophic organisms and organisms that use or "take-up" methane. Methane-utilizing microorganisms may be confined in a microorganism holding tank containing methane-utilizing microorganisms and a microorganism growth-culture medium. They may also be present in a biofiltration system containing methane-utilizing microorganisms wherein microorganisms either are or are not attached to a microorganism support substrate and are continuously or intermittently contacted with a microorganism growth-culture medium. They may also be used in a bioreactor containing methane-utilizing microorganisms and a microorganism growth-culture medium wherein the growth-culture medium is in liquid, foam, solid, semi-solid, or any other suitable form and methane-utilizing microorganisms are naturally-occurring and/or genetically engineered and may or may not have been selectively inserted as part of a pre-determined microbial consortium. While the use of specified microorganism consortium may provide some benefits, a non-specified and naturally-equilibrating consortium of one or more microorganisms may also be employed. Typical examples of methane-utilizing microorganisms useful in several embodiments of the present invention include, but are not limited to, bacteria and yeast.

Suitable yeasts include species from the genera *Candida, Hansenula, Torulopsis, Saccharomyces, Pichia*, 1-*Debaryomyces, Lipomyces, Cryptococcus, Nematospora*, and *Brettanomyces*. The preferred genera include *Candida, Hansenula, Torulopsis, Pichia*, and *Saccharomyces*. Examples of suitable species include: *Candida boidinii, Candida mycoderma, Candida utilis, Candida stellatoidea, Candida robusta, Candida claussenii, Candida rugosa, Brettanomyces petrophilium, Hansenula minuta, Hansenula saturnus, Hansenula californica, Hansenula mrakii, Hansenula silvicola, Hansenula polymorpha, Hansenula wickerhamii, Hansenula capsulata, Hansenula glucozyma, Hansenula henricii, Hansenula nonfermentans, Hansenula philodendra, Torulopsis candida, Torulopsis bolmii, Torulopsis versatilis, Torulopsis glabrata, Torulopsis molishiana, Torulopsis nemodendra, Torulopsis nitratophila, Torulopsis pinus, Pichia farinosa, Pichia polymorpha, Pichia membranaefaciens, Pichia pinus, Pichia pastoris, Pichia trehalophila, Saccharomyces cerevisiae, Saccharomyces fragilis, Saccharomyces rosei, Saccharomyces acidifaciens, Saccharomyces elegans, Saccharomyces rouxii, Saccharomyces lactis*, and/or *Saccharomyces fractum*.

Suitable bacteria include species from the genera *Bacillus, Mycobacterium, Actinomyces, Nocardia, Pseudomonas, Methanomonas, Protaminobacter, Methylococcus, Arthrobacter, Methylomonas, Brevibacterium, Acetobacter, Methylomonas, Brevibacterium, Acetobacter, Micrococcus, Rhodopseudomonas, Corynebacterium, Rhodopseudomonas, Microbacterium, Achromobacter, Methylobacter, Methylosinus*, and *Methylocystis*. Preferred genera include *Bacillus, Pseudomonas, Protaminobacter, Micrococcus, Arthrobacter* and/or *Corynebacterium*. Examples of suitable species include: *Bacillus subtilus, Bacillus cereus, Bacillus aureus, Bacillus acidi, Bacillus urici, Bacillus coagulans, Bacillus mycoides, Bacillus circulans, Bacillus megaterium, Bacillus licheniformis, Pseudomonas ligustri, Pseudomonas orvilla, Pseudomonas methanica, Pseudomonas fluorescens, Pseudomonas aeruginosa, Pseudomonas oleovorans, Pseudomonas putida, Pseudomonas boreopolis, Pseudomonas pyocyanea, Pseudomonas methylphilus, Pseudomonas brevis, Pseudomonas acidovorans, Pseudomonas methanoloxidans, Pseudomonas aerogenes, Protaminobacter ruber, Corynebacterium simplex, Corynebacterium hydrocarbooxydans, Corynebacterium alkanum, Corynebacterium oleophilus, Corynebacterium hydrocarboclastus, Corynebacterium glutamicum, Corynebacterium viscosus, Corynebacterium dioxydans, Corynebacterium alkanum, Micrococcus cerificans, Micrococcus rhodius, Arthrobacter rufescens, Arthrobacter parafficum, Arthrobacter citreus, Methanomonas methanica, Methanomonas methanooxidans, Methylomonas agile, Methylomonas albus, Methylomonas rubrum, Methylomonas methanolica, Mycobacterium rhodochrous, Mycobacterium phlei, Mycobacterium brevicale, Nocardia salmonicolor, Nocardia minimus, Nocardia corallina, Nocardia butanica, Rhodopseudomonas capsulatus, Microbacterium ammoniaphilum, Archromobacter coagulans, Brevibacterium butanicum, Brevibacterium roseum, Brevibacterium flavum, Brevibacterium lactofermentum, Brevibacterium paraffinolyticum, Brevibacterium ketoglutamicum*, and/or *Brevibacterium insectiphilium*.

The term "microorganism growth-culture medium" shall be given its ordinary meaning and shall also refer to any medium promoting the growth of microorganisms. It shall also refer to any substrate, aside from methane, which microorganisms oxidize or otherwise break down. It shall also refer to any substrate or material that concentrates methane, preferentially sequesters methane, "traps" methane, increases the solubility and/or availability of methane, and/or otherwise enables the enhanced breakdown, oxidation, and/or utilization of methane by microorganisms. The term "microorganism growth-culture medium" includes, but is not limited to, any substrate and/or microorganism immobilization means, such as liquid, semi-liquid, gas, particulate, ceramic, foam, plastic, alginate gel, methanol-enriched, copper-enriched, clay, nutrient, or other appropriate growth-culture medium. In one preferred embodiment, this growth culture medium comprises aqueous solution containing water, nitrogen, ammonium, trace minerals, and other well-known microorganism growth-culture medium components necessary for the growth and reproduction of methane-utilizing bacteria. In another preferred embodiment, this growth culture medium comprises a microorganism immobilization means, such as organic or inorganic particles, on which a liquid or semi-liquid mineral medium solution is continuously or periodically contacted and on which microorganisms are attached. In another preferred embodiment, this growth-culture medium comprises waste organic materials, which methane-utilizing microorganisms may or may not break down to produce a byproduct of organic materials that may or may not be useful. In another preferred embodiment, this growth-culture medium comprises a liquid foam substrate. In yet another preferred embodiment, this growth-culture medium is mixed with various materials which methane-utilizing microorganisms may or may not convert to more desirable materials. Examples of various materials include, but are not limited to, toluene, trichloroethylene (TCE), propylene, and agricultural byproduct materials which microorganisms may preferentially breakdown or oxidize.

In one embodiment of the present invention, the method of the subject invention involves conveying enteric fermentation methane to an apparatus situated entirely on the body of a ruminant animal which mutually-exposes methane-utilizing microorganisms, enteric fermentation methane, and a microorganism growth-culture medium, causing methane-utilizing microorganisms to grow using enteric fermentation methane as a source of carbon and/or energy. Preferred embodiments of the invention are described below and illustrated by FIGS. 1, 2, and 3.

FIG. 1 is a side perspective view of an apparatus used to carry out a process in accordance with the invention. In this illustration, all of the means necessary for carrying out a process in accordance with the invention are maintained and situated entirely on the body of ruminant animal, including means for conveying ruminant animal exhalation, and the exhalation methane therein, to a means for mutually-exposing enteric fermentation methane, methane-utilizing microorganisms, and a microorganism growth-culture medium, as well as a means for harvesting the product of methane-utilizing microorganism growth.

In FIG. 1, exhalation collection tubes 15a and 15b are situated one on either side of the head of ruminant animal 14. Tubes 15a and 15b are held in place by stationary head harness 16 and lead up to the nostrils of ruminant animal 14. Tubes 15a and 15b run from the nostrils of ruminant animal 14 to where they both converge into exhalation collection tube convergence T-pipe 18. T-pipe 18 connects to exhalation inflow tube 19, which leads into permanent exhalation conveyance structure 20. Structure 20 is described in further detail by FIGS. 2A and 2B. Structure 20 is held in place on the back of ruminant animal 14 by stabilizing leg straps 17a, 17b, 17c, and 17d, as illustrated.

Figure 2A:
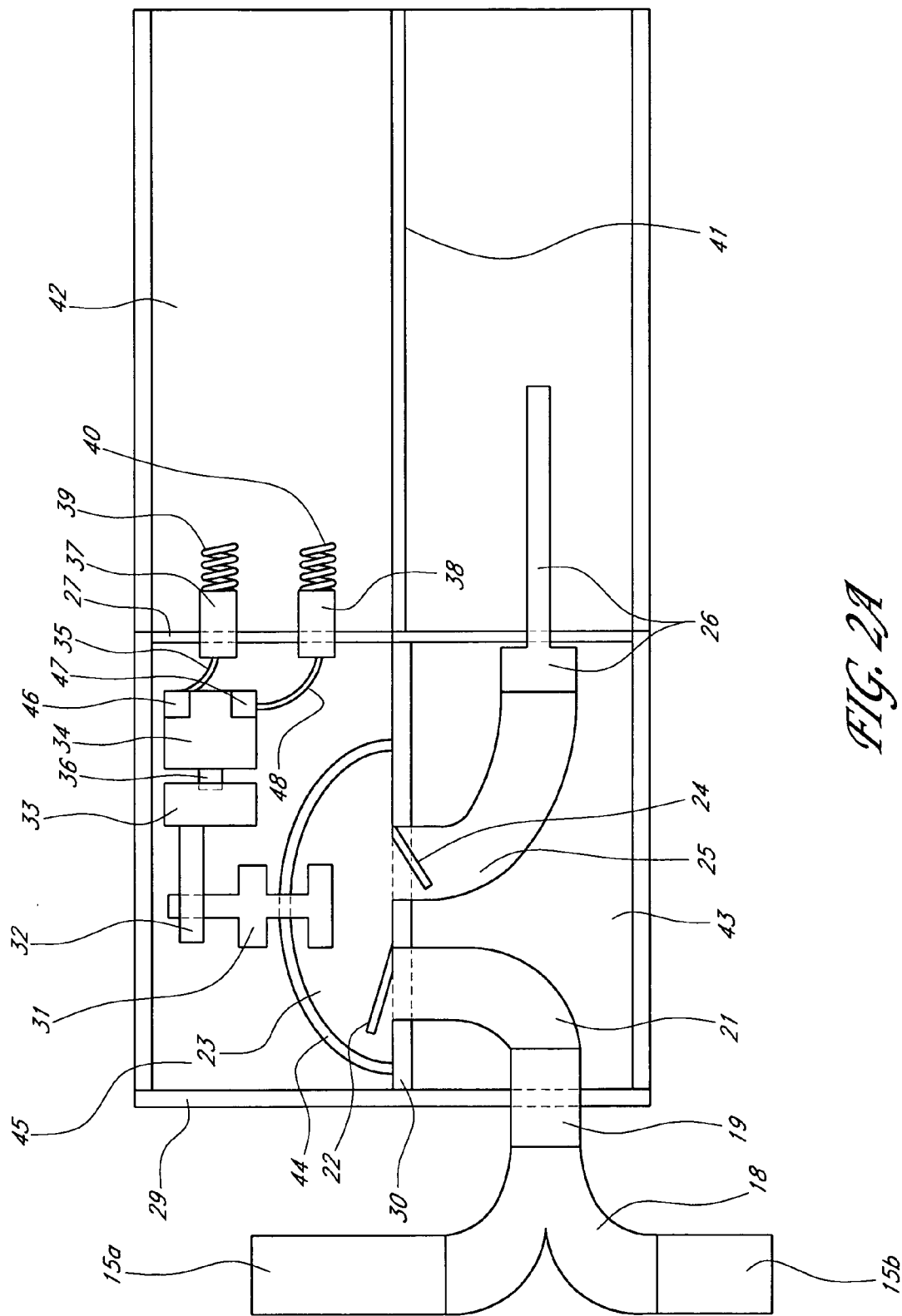
FIGS. 2A, 2B, 3A, and 3B describe this apparatus in greater detail.
Figure 2B:
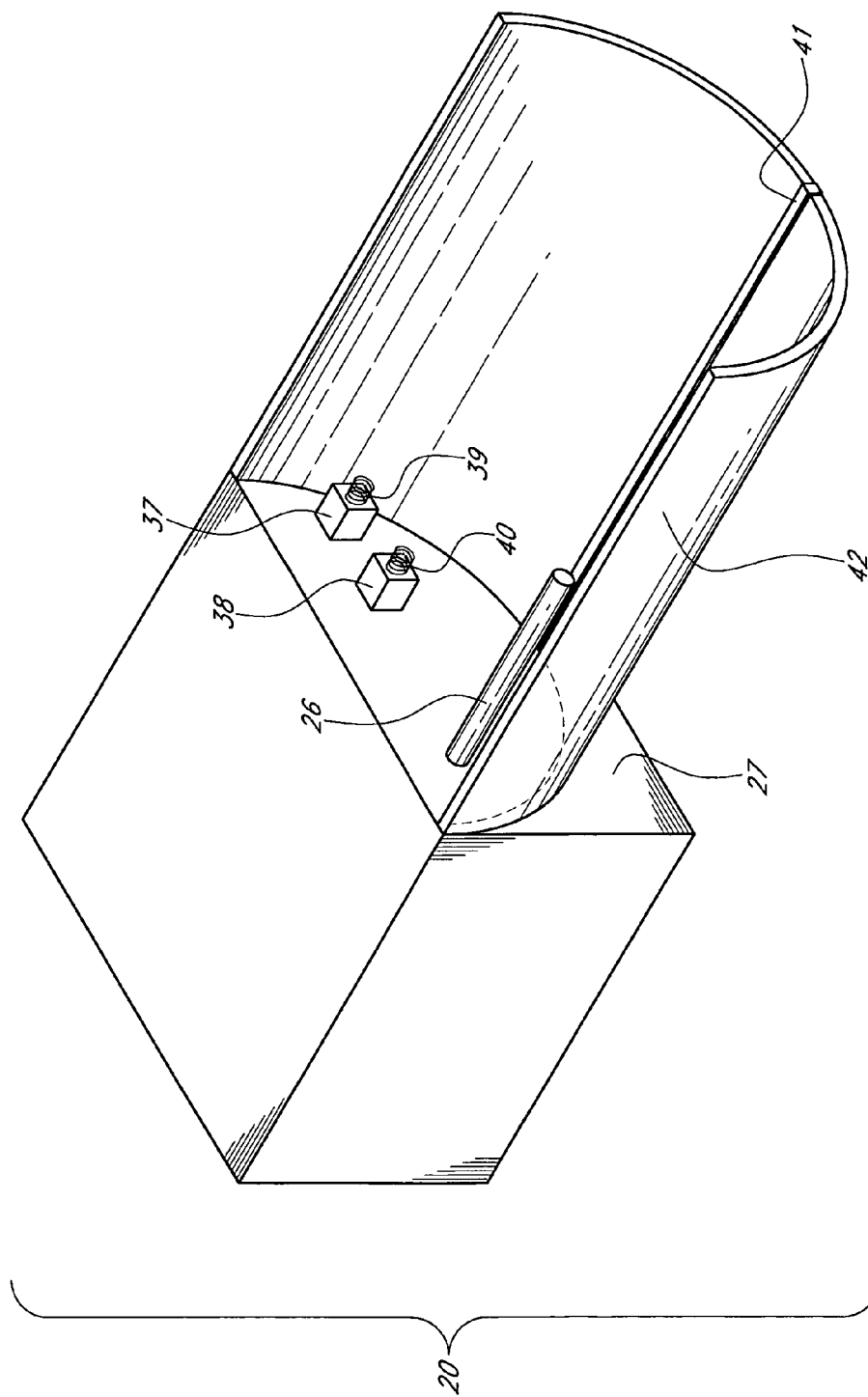

FIG. 2A is a top cross-sectional view of structure 20, and FIG. 2B is a side perspective view of structure 20. Tube 19 passes through air pump housing front wall 29 and leads into exhalation flow pipe chamber 43. Inside chamber 43, tube 19 connects to inflow pump chamber tube 21, which leads through chamber 43, through air pump housing middle wall 30, and into diaphragm-enclosed chamber 23. Where tube 21 opens into chamber 23 is inflow one-way flap sphincter 22, which, being a one-way flap, allows air to travel into chamber 23, but does not allow air to travel from chamber 23 into tube 21.

Chamber 23 is enclosed by rubber diaphragm 44. The open end of diaphragm 44 is attached to wall 30 so that an air-tight seal is made, and chamber 23 is formed. Diaphragm pump plunger 31 is inserted through and into diaphragm 44 on the side of diaphragm 44 farthest from wall 30. Plunger 31 extends out of diaphragm 44 to where it is joined perpendicularly to rotational gear tooth 32, which is attached to rotational gear 33. Gear 33 is mounted on motor axle 36, which leads into direct-current rotational motor 34. Motor 34 is located inside exhalation motor pumping chamber 45. Positive motor electrical terminal 46 is connected to permanent structure positive conduction plate 37 by positive electrical conduction wire 35. Negative motor electrical terminal 47 is connected to permanent structure negative conduction plate 38 by negative electrical conduction wire 48. Plate 37 and plate 38 are mounted on air pump housing back wall 27 with portions of each plate protruding through and outside of wall 27. Connected to the end of plate 37 on the end farthest from chamber 45 is positive conduction continuation spring 39. Connected to the end of permanent structure negative conduction plate 38 on the end farthest from chamber 45 is negative continuation spring 40. Structurally, an electric current can now flow from spring 39 to terminal 46 as well as from spring 40 to terminal 47.

Returning to chamber 23, outflow one-way flap sphincter 24 leads out from chamber 23 and into outflow pump chamber tube 25. Sphincter 24 allows air to travel out of chamber 23, but it does not allow air to travel from tube 25 into chamber 23. Tube 25 runs from chamber 23, through wall 30, and through chamber 43 to where it finally connects with outflow insertion needle 26. Needle 26 runs from the inside of chamber 43, protrudes through wall 27, and extends beyond wall 27 directly away from tube 19. Needle 26 is open on the end farthest from tube 25.

Half-cylindrical shell 42 is attached to wall 27. The orientation of shell 42 is depicted in FIG. 2B. Running the length of shell 42 is inlaid guidance groove 41. As will be described later, groove 41 has the purpose of guiding removable microorganism containment capsule 99 into correct orientation with needle 26, spring 39, and spring 40. Capsule 99 is described in greater detail in FIGS. 3A and 3B.

Figure 3A:
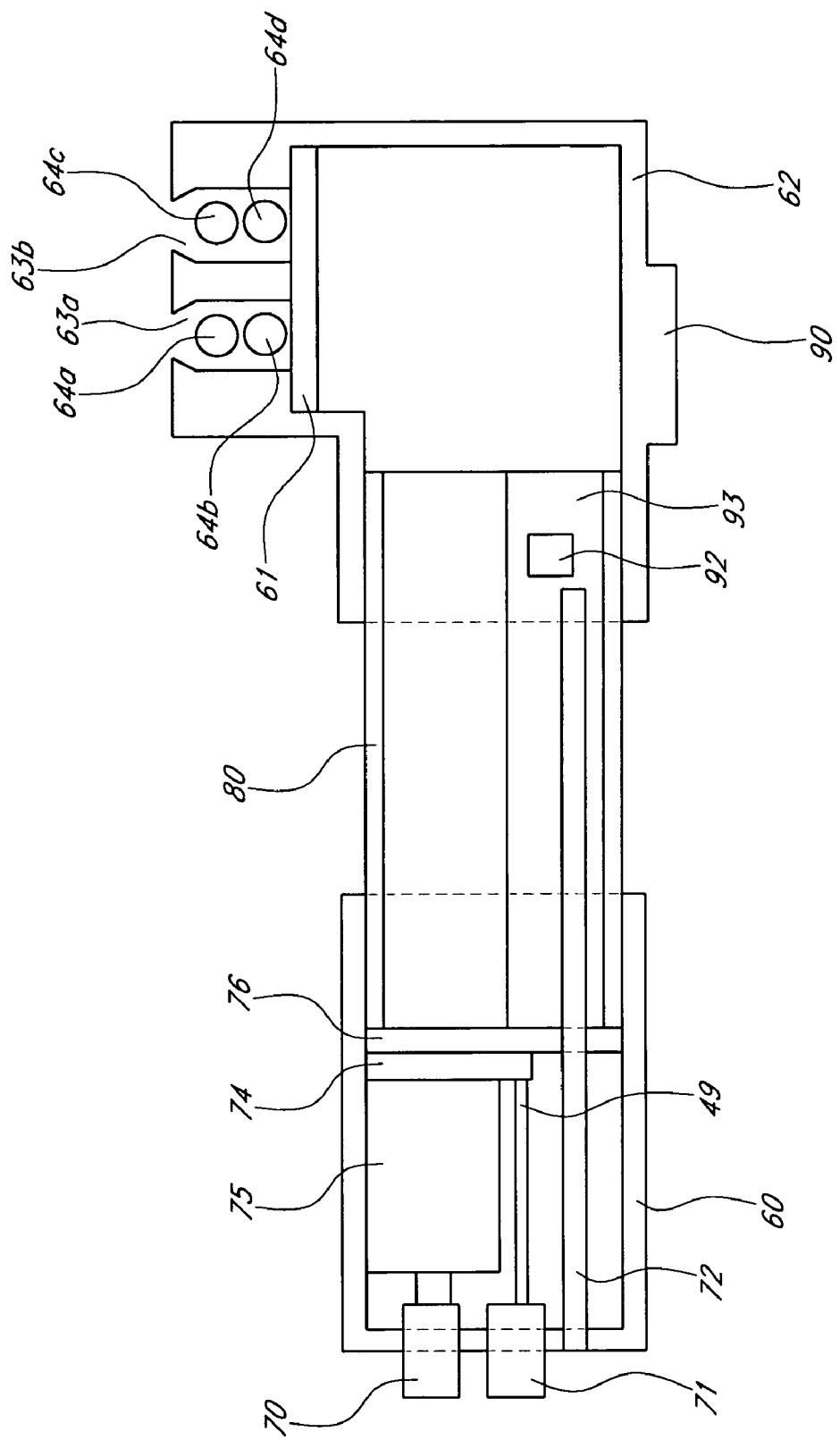
Figure 3B:
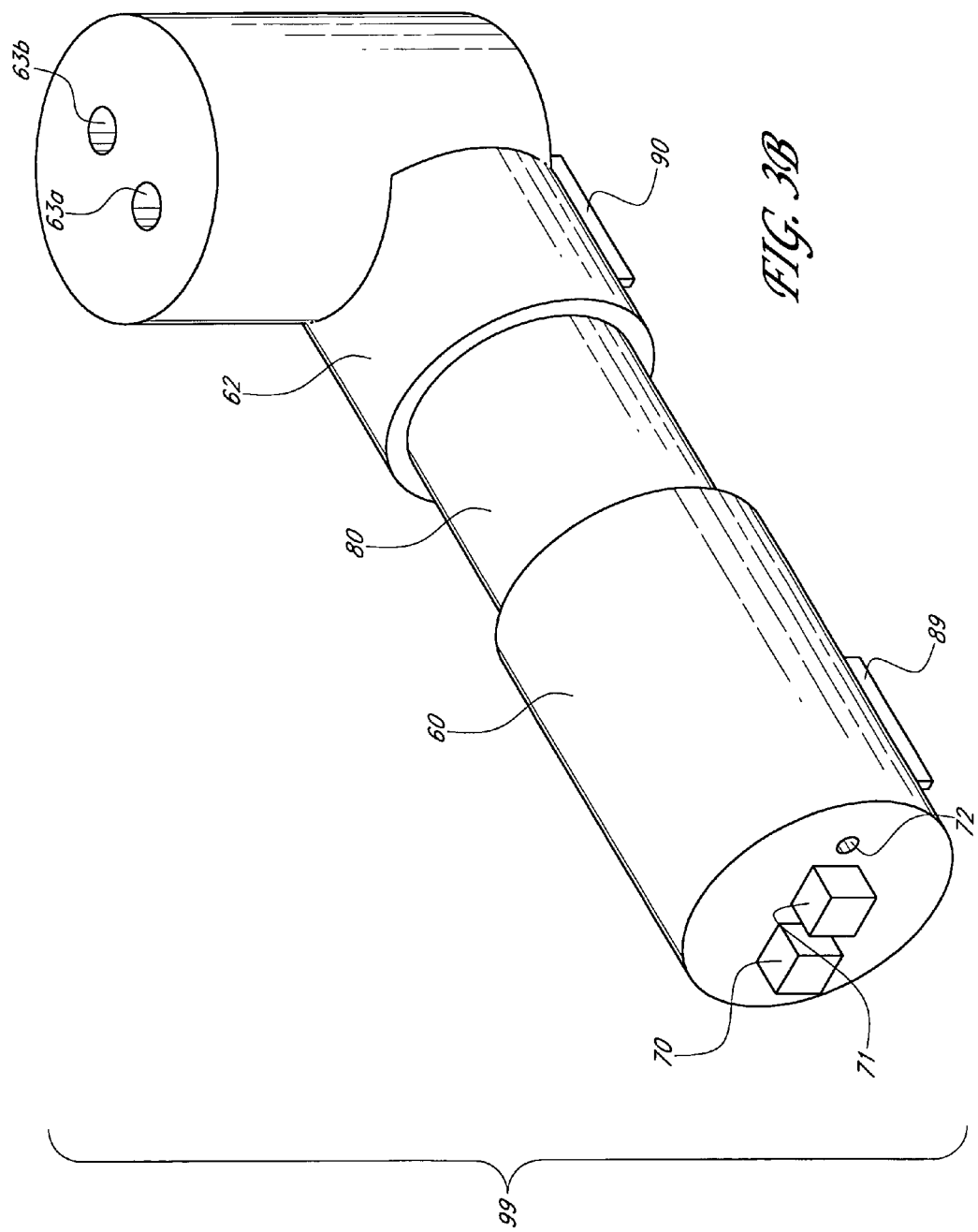

FIG. 3A and FIG. 3B depict capsule 99. Specifically, FIG. 3A is a side cross-sectional view of capsule 99, and FIG. 3B is a side perspective view of capsule 99. Structure 20 is designed to support and feed ruminant animal exhalation (and the methane contained therein) into capsule 99. Designed accordingly, capsule 99 is described in three parts: threaded inflow attachment pipe 60, threaded outflow attachment pipe 62, and microorganism growth capsule pipe 80. Capsule 99, as a whole, consists of each of these three pieces connected together, as will be described.

Pipe 80 is threaded on the outer side of both ends and contains methane-utilizing microorganisms 92 and microorganism growth-culture medium 93. In the present embodiment, 5 grams of *Methylococcus capsulatus*, methane-utilizing microorganisms which can be obtained from a number of biological supply depots (including Chang Bioscience, located at 125 Cambon Drive #6H, San Francisco, Calif. 94132) are placed in an aqueous microorganism growth-culture medium containing ammonium, nitrogen, and mineral salts.

Attached to one end of pipe 80 is pipe 60. Attached on the other end of pipe 80 is pipe 62. Pipe 60 houses D-size battery 75, which is situated between removable capsule positive electrical conduction terminal 70, removable capsule negative electrical conduction plate 74, and inflow attachment pipe inner wall 76. Plate 74 rests against wall 76 and sits adjacent to battery 75. Terminal 70 sits adjacent to battery 75 and protrudes through the front side of pipe 60. Similarly, terminal 71 protrudes through the front side of pipe 60 from the inside of pipe 60. Capsule negative electrical conduction wire 49 runs from terminal 71 to plate 74. Running from the outer edge of the front side of pipe 60, passing through wall 76, and extending beyond wall 76 into pipe 80 is air dispersion capillary tube 72. Tube 72 is a solid tube except for the portion extending into pipe 80, which contains tiny capillary holes in its walls that allow air to pass out of tube 72 but do not allow medium 93 to pass into tube 72. Tube 72 is open at the end meeting the outer edge of the front side of pipe 60, and closed at its opposite end. Attached to the outside of pipe 60 is inflow guidance ridge 89, a solid piece of material which will eventually fit into groove 41 illustrated in FIG. 2A and FIG. 2B.

Attached to pipe 80 on the end opposite pipe 60 is pipe 62. Pipe 62 is an elbow-shaped pipe that allows air to escape after it has passed through the small holes in the walls of tube 72. Pipe 62 is a hollow piece of piece of pipe at the end where it is connected to pipe 80, though, at its other end, pipe 62 is a solid piece of pipe. Wire mesh grating 61 is located inside pipe 62 at the border of where pipe 62 turns from hollow to solid. Still inside of pipe 62, adjacent to grating 61 in the solid portion of pipe 62, leak prevention holes 63a and 63b are drilled through the solid piece of pipe 62. Inside of hole 63a are plug balls 64a and 64b. Inside of hole 63b are plug balls 64c and 64d. Balls 64a, 64b, 64c, and 64d are rubber balls which can float on the surface of medium 93. Holes 63a and 63b are partially blocked at both the ends farthest and the ends closest to the hollow portion of pipe 62. Holes 63a and 63b are partially blocked by grating 61 at the end closest to the hollow portion of pipe 62. While the diameters of holes 63a and 63b are constant throughout, the diameters decrease at the ends farthest from the hollow portion of pipe 62 such that a single ball (64a or 64c) cannot pass through that end. Similar to ridge 89, outflow guidance ridge 90, which is able to slide into groove 41, is located on the outside of pipe 62.

The following is a description of one method by which an apparatus is used to carry out a process in accordance with one embodiment of the invention.

First, structure 20 is situated on the back of ruminant animal 14 using straps 17a, 17b, 17c, and 17d. Next, harness 16 is attached to the head of ruminant animal 14, and tubes 15a and 15b are connected to harness 16 such that tubes 15a and 15b lead from T-pipe 18 up to the nostrils of ruminant animal 14.

Second, capsule 99 is placed into shell 42 of structure 20. This is accomplished by inserting ridge 89 and ridge 90 on capsule 99 into groove 41 inlaid in shell 42 of structure 20. With capsule 99 aligned with structure 20, capsule 99 is slid towards wall 27 up to the point where needle 26 is inserted into tube 72, and spring 39 and spring 40 are placed, respectively, into contact with terminal 70 and terminal 71. With terminal 70 and terminal 71 placed into contact with spring 39 and spring 40, respectively, an electrical current now runs from battery 75 in capsule 99 to motor 34 in structure 20. Specifically, a positive electrical current runs from battery 75, through terminal 70, through spring 39, through plate 37, though wire 35, to terminal 46. A negative electrical current runs from battery 75, through plate 74, through wire 49, through terminal 71, through spring 40, through plate 38, through wire 48, to terminal 47.

With an electrical current running from battery 75 to motor 34, axle 36 on motor 34 begins to rotate rapidly. As axle 36 rotates, gear 33 and gear tooth 32 also rotate rapidly, which in turn causes plunger 31 to rapidly push and pull diaphragm 44. With diaphragm 44 oscillating towards and away from wall 30, the motion of diaphragm 44 causes air to flow from tubes 15a and 15b, into chamber 23, and into needle 26. To expand, air is pulled through tubes 15a and 15b, through T-pipe 18, through tube 19, through tube 21, past sphincter 22, through chamber 23, past sphincter 24, through tube 25, and into needle 26.

With capsule 99 inserted, as described above, into structure 20, air now travels from needle 26 into tube 72. Since tube 72 is blocked at the end located in pipe 80 and since air cannot travel from tube 72 back into chamber 23, air is forced out through the tiny holes which exist in the walls of tube 72. To reiterate a detail mentioned above, tiny holes exist in the walls of tube 72 only where tube 72 extends into pipe 80. The result is that air is conveyed from needle 26, through tube 72, and into pipe 80. Eventually, with no other means of escape, the air inside pipe 80 flows into the hollow portion of pipe 62, past grating 61, into holes 63a and 63b, past plug balls 64a, 64b, 64c, and 64d, out of holes 63a and 63b.

The result of this conveyance of air is that as ruminant animal 14 exhales, this exhalation, as well as exhalation methane therein, is conveyed and directed into tubes 15a and 15b, which are situated just above the nostrils of ruminant animal 14. Exhalation methane now travels through tubes 15a and 15b to needle 26. With capsule 99 inserted, as described above, into structure 20, exhalation methane of ruminant animal 14 travels through needle 26 into pipe 80.

Pipe 80 contains microorganisms 92 and medium 93, and when exhalation methane is conveyed into pipe 80, microorganisms 92 grow and reproduce using this exhalation methane as a source of carbon and/or energy. Put differently, exhalation methane, microorganisms 92, and medium 93 are mutually-exposed in pipe 80. Thus, as more exhalation methane from ruminant animal 14 is exposed to microorganisms 92 in medium 93, microorganisms 92 grow and reproduce using exhalation methane as a source of carbon and/or energy. All excess gases, including waste carbon dioxide and waste exhalation methane, exit capsule 99 as described above.

Although medium 93 is an aqueous medium, holes 63a and 63b, balls 64a, 64b, 64c, and 64d, and grating 61 act together to prevent medium 93 from spilling or escaping out of capsule 99. Specifically, since plug balls 64a, 64b, 64c, and 64d are designed to float on the surface of medium 93, if medium 93 travels past grating 61 and moves into holes 63a and/or 63b, balls 64a and 64c will plug the small-diameter end of holes 63a and 63b, respectively, before the aqueous medium 93 can pass out of capsule 99.

The process continues when, after a certain amount of time (in this embodiment approximately 7 days) it is determined that microorganisms 92 within capsule 99 are no longer growing at optimal rates or have stopped growing completely, and capsule 99 is removed from structure 20. The microorganism growth process is re-started and continued simply by replacing previously-used capsule 99 with a new apparatus structurally identical to capsule 99 containing new methane-utilizing microorganisms and a new microorganism growth-culture medium. The process may also be continued by re-using capsule 99 and, after removing all or most of microorganisms 92 and medium 93, filling it with new microorganism growth-culture medium and an optimal number of new or previously used methane-utilizing microorganisms. In such a manner, exhalation methane is continually used as a source of carbon and/or energy for the growth and harvesting of methane-utilizing microorganisms.

Finally, microorganisms 92, having been grown in capsule 99 using exhalation methane as a source of carbon and/or energy, are removed from capsule 99 and harvested as useful biomass. (*Methylococcus capsulatus* has a biomass which consists of about seventy percent protein by weight). Such biomass can be processed and sold as a nutritional foodstuff or converted into other useful products, such as adhesives or cosmetics.

Figure 4:
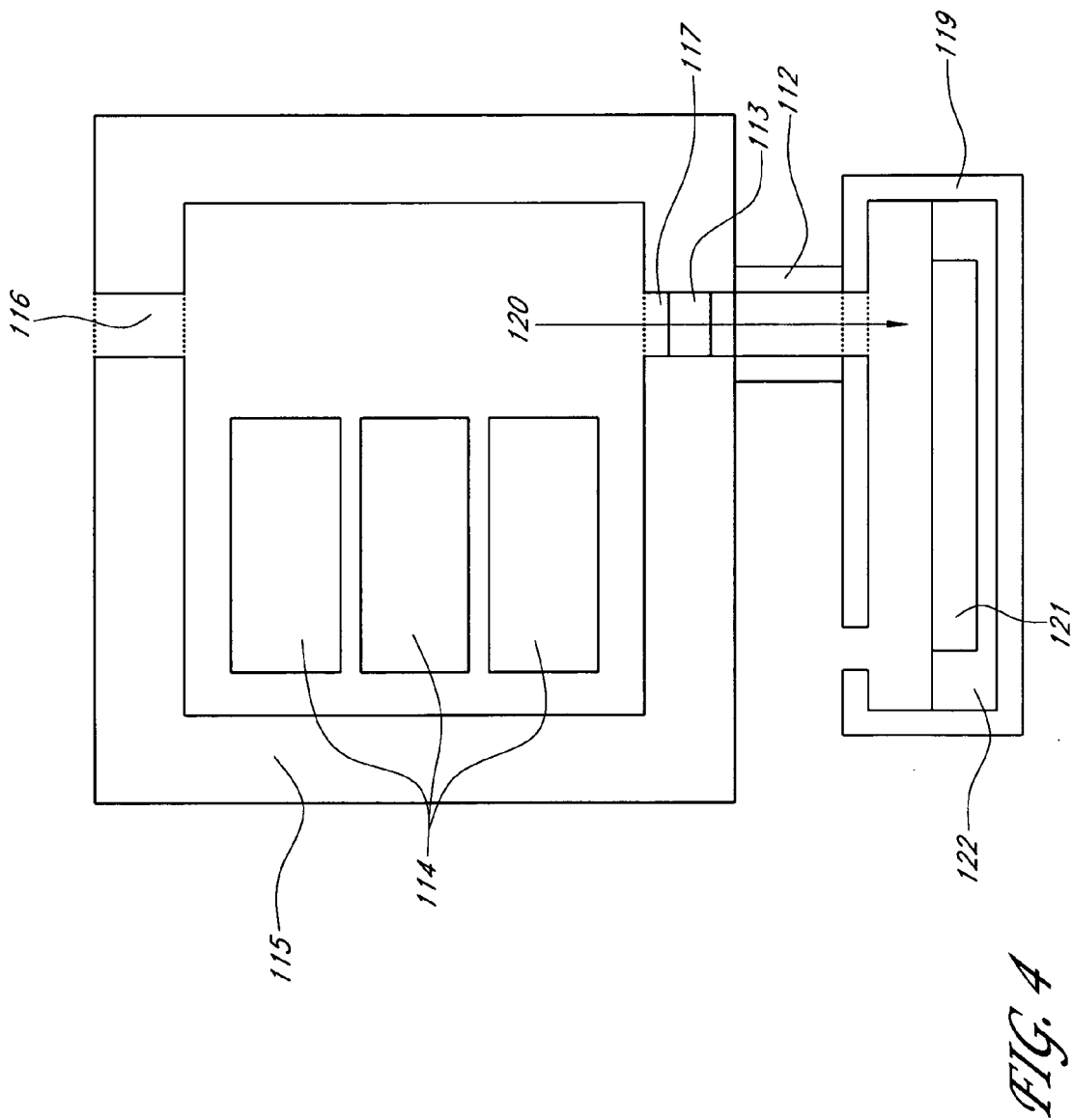
FIG. 4 is a schematic of a preferred embodiment of a process carried out in accordance with one embodiment of the invention.

In one preferred embodiment, as detailed by FIG. 4, "mutual-exposure means" shall be given its ordinary meaning and shall also refer to any apparatus housing, holding, or containing a methane-consumption system such as microorganisms, fuel cells, or microturbines. In one embodiment, this apparatus comprises a holding tank containing methane-utilizing microorganisms and a microorganism growth-culture medium. In another embodiment, this apparatus comprises the materials housing and/or supporting the operation of a reverse-flow reactor, an engine, a fuel cell, and/or a microturbine. In another embodiment, this means comprises a temperature-controlled, stainless-steel cylindrical bioreactor apparatus containing, holding, or enclosing methanotrophic microorganism growth-culture medium and methane-utilizing microorganisms, into which enclosure air, including ammonia and ruminant animal methane, is fed, conveyed, or directed, which subsequently allows microorganisms to grow and reproduce utilizing ruminant animal methane as a source of carbon and/or energy for growth. In another embodiment, the growth of random, non-specified, genetically-engineered, pre-determined, and/or non-pre-determined methane-utilizing microorganisms in such a bioreactor may be used to lower the concentration of ammonia in enclosure air. In another embodiment, means are provided to trap or capture dust and other airborne matter in the enclosure air such that any or all of such matter does not actually contact a methane-consumption means, such as methane-utilizing microorganisms or a methane-driven microturbine, reverse-flow reactor, or fuel cell. In this way, a mutual-exposure means may be used not only to carry out methane-driven processes, but also to lower the dust, ammonia, and/or airborne matter contents in enclosure air.

Embodiments of the subject invention pertain to the utilization of the enteric fermentation methane produced by ruminant animals for the production of methane-based goods. More particularly, embodiments of the present invention pertain to the process of utilizing ruminant animal enteric fermentation methane emissions in which the method comprises: (a) providing one or more ruminant animals, (b) providing enteric fermentation-derived methane gas that has been emitted by the animals, including air containing said methane, (c) providing means to capture, consolidate, and/or direct the methane, including an enclosure means to enclose the animals, the air, and the methane contained in the air, and, preferentially, a ventilation means to direct the air, (d) providing a methane-consumption means which can use the methane as a source of carbon and/or energy for the induction of a methane-based process and/or for the production of methane-based goods, and (e) contacting the methane with the methane-consumption means to cause the methane-consumption means to oxidize, consume, and/or otherwise utilize the methane for the operation of a methane-based process or for the production of one or more methane-based products, including methane-utilizing microorganisms, heat, and/or electricity. Another embodiment of the invention pertains to the process wherein: a) one more ruminant animals are fully or partially enclosed by a well-known enclosure means, such as a barn, and b) air contained in an ruminant animal enclosure means, including the enteric fermentation methane contained therein, is further directed and exposed to a methane-consumption system, whereby enteric fermentation methane is used as a novel source of carbon and/or energy for the production of heat, electricity, or, as in one preferred embodiment, methane-utilizing microorganisms.

In one preferred embodiment, the method of the subject invention involves contacting enteric fermentation methane contained within enclosed barn air with a microbiological methane-consumption system, wherein enteric fermentation methane, methane-utilizing microorganisms, and a microorganism growth-culture medium are mutually-exposed, causing methane-utilizing microorganisms to grow using enteric fermentation methane as a source of carbon and/or energy.

FIG. 4 is a flow chart of a process carried out in accordance with the invention. In the schematic, ruminant animal 114 is situated in enclosure means 115, whereby ruminant animal 114 is substantially enclosed, isolated, and contained by and in enclosure means 115. In one preferred embodiment, enclosure means 115 includes a barn with four sidewalls and a roof.

Enclosure means 115 contains enclosure air 120. Enclosure means 115 is equipped with air inlet 116 and air outlet 117, through which air, gases, and other airborne materials are substantially confined to enter and exit enclosure means 115, respectively. In one preferred embodiment, air inlet 116 consists of a spatial opening, such as a window, in a side wall of enclosure means 115, and air outlet 117 consists of a spatial opening housing ventilation means 113, through which air, gases, and other airborne material exit out of inside enclosure means 115. In one preferred embodiment, ventilation means 113 consists of a well-known ventilation fan that is used to pull air into enclosure means 115 through air inlet 116 and convey air out of enclosure means 115 through air outlet 117. Consolidation means 112 is a duct that directs enclosure air 120 coming out of air outlet 117 in such a way that it can be contacted with confined methane-utilizing microorganisms 121. In the embodiment depicted, mutual-exposure means 119 is a holding tank containing a methane-consumption means, embodied as methane-utilizing microorganisms 121, and microorganism growth-culture medium 122. In the embodiment depicted, methane-utilizing microorganisms 121 are present in growth-culture medium 122 at a concentration of 20 grams of microorganisms per liter of medium, and consist of methane-utilizing microorganisms such as *Methylococcus capsulatus* that can be obtained from any number of well known biological supply depots (including Chang Bioscience, located at 125 Cambon Drive #6H, San Francisco, Calif. 94132). Growth-culture medium 122, as herein embodied, is an aqueous medium containing suitable ammonium, mineral salts, and other well-known growth-culture components, which support the growth of methane-utilizing microorganisms 121.

The following is a description of one method by which to carry out a process in accordance with one embodiment of the invention. First, ruminant animal 114 is enclosed by enclosure means 115, and ruminant animal emits methane gas into enclosure air 120 through processes associated with enteric fermentation. Next, through the force of ventilation means 113, air is conveyed into enclosure means 115 through air inlet 116, through enclosure means 115, and out of enclosure means 115 through air outlet 117. Enclosure air 120 containing enteric fermentation methane is next conveyed out of air outlet 117, through consolidation means 112 to be contacted with methane utilizing microorganisms 121 in mutual-exposure means 119 through the force created by ventilation means 113. Inside mutual-exposure means 119, enteric fermentation methane contained within enclosure air 120 is exposed to methane-utilizing microorganisms 121 and growth-culture medium 122, causing methane-utilizing microorganisms 121 to grow and reproduce using enteric fermentation methane as a source of carbon and/or energy. The process continues when, after a certain amount of time (in this embodiment approximately 7 days) it is determined that methane-utilizing microorganisms 121 within mutual-exposure means 119 are no longer growing at optimal rates, and the microorganism growth process is augmented by removing portions of growth-culture medium 122 and methane-utilizing microorganisms 121 from mutual-exposure means 119 and adding new portions of growth-culture medium 122 and/or methane-utilizing microorganisms 121. In such a manner, enteric fermentation methane is continually used as a source of carbon and/or energy for the continuous growth and harvesting of methane-utilizing microorganisms. Finally, methane-utilizing microorganisms 121, having been grown in mutual-exposure means 119 using enteric fermentation methane as a source of carbon and/or energy, are removed from mutual-exposure means 119 and harvested as useful biomass. Such biomass can be processed and sold as a range of useful biomass-based products.

In one preferred embodiment, as described earlier, ventilation means 113 are employed to move 10 cubic feet of enclosure air 120 out of air outlet 117 each minute, such that fresh air enters into enclosure means 115 at the same rate, and enclosure air 120 is cooled by the air cooling means described earlier. As described, a dairy cow produces approximately 150 kilograms of methane per year, which correlates to the production of approximately 0.4 liters per minute of enteric fermentation methane. Thus, by enclosing ruminant animal 114 with enclosure means 115 and employing ventilation means 113, the concentration of methane in enclosure air 120 conveyed into mutual-exposure means is at least 0.1% methane by volume, or 1000 parts per million. By decreasing or increasing ventilation rates, the concentration of methane in enclosure air 120 increases or decreases accordingly. Methane-utilizing microorganisms are able to grow and reproduce using methane as a source of carbon and/or energy in an environment wherein the concentration of methane-in-air is at least 1.7 parts per million. Thus, methane-utilizing microorganisms 121 are enabled to grow and reproduce using enteric fermentation methane as a novel source of energy in one preferred embodiment.

Several embodiments of the present invention pertain to the utilization of enteric fermentation as a novel source of energy for the production of methane-based goods in a confined methane-consumption apparatus existing outside the digestive tract of a ruminant animal. There are a number of potential methods that can be used to carry out a process in accordance with embodiments of the invention. In particular, there are a number of methods that can be utilized to capture enteric fermentation methane with enclosure and ventilation means and mutually-expose enteric fermentation methane and a methane-consumption means for the purpose of causing enteric fermentation methane to be utilized as a source of carbon and/or energy.

In some embodiments, such methods include, but are not limited to, providing methane-consumption means to convert enteric fermentation methane into heat and/or electricity. It is known that the utilization of methane is possible at methane-in-air volumetric concentrations down to 0.1% methane-in-air, specifically by catalytic and thermal flow-reversal reactors, and systems such as these could be used as a means to utilize enteric fermentation as a viable, low-concentration source of energy in accordance with the invention. Specifically, microturbines, fuel cells, reverse-flow reactors and other means capable of utilizing methane at low concentrations can be used as a methane-consumption means in accordance with the invention, allowing enclosure air to be used in an unadulterated state as viable feedstock fuel. Gas concentrators that increase methane-in-air concentrations of exhaust gas could also be employed to increase methane concentrations to levels more suitable for use by a range of methane-consumption means. Thus, although one preferred embodiment details the use of methane-utilizing microorganism as a preferred methane-consumption means, in another embodiment, any number of methane-consumption means may be employed in accordance with embodiments of the invention to convert enteric fermentation methane into useful products such as heat and/or electricity.

In some embodiments, such methods also include the combined use of non-enteric fermentation methane and enteric fermentation methane in or by a methane-consumption means, such that enteric fermentation methane can be partially used to drive one or more methane-consumption means, such as fuel cells, turbines, microturbines, methane-utilizing microorganisms, and other methane-based systems. Such alternative sources of supplemental methane might include: methane from agricultural manure digesters, agricultural manure holding structures, landfills, coal mines, wastewater treatment facilities, and/or natural gas.

In some embodiments, such methods further include the utilization of a chemical-based methane-consumption means to use enteric fermentation methane as a source of carbon and/or energy. Specifically, a number of methods are well known to convert methane into industrial feedstock products, such as methanol, through the mutual exposure of methane and various chemicals under a variety of conditions. Suitable chemical processing methods of this nature could be applied to enteric fermentation methane in accordance with the principles of the invention, especially through the combined use of enteric fermentation methane and alternative sources of methane, as enumerated above, to increase the yields, viability, and efficiency of the process.

In some embodiments, such methods also include using methane-utilizing microorganisms to simultaneously reduce both ammonia and methane emissions from ruminant animal feedlots. In one preferred embodiment, enclosure air 120 will likely contain varying amounts of ammonia gas. It is well known that contacting ammonia gas with liquid water changes ammonia gas into aqueous ammonium, as would occur in mutual-exposure means 119 of one preferred embodiment listed above when enclosure gas 120 is contacted with growth-culture medium 122. It is well known that methane-utilizing microorganisms utilize ammonium in water as a source of nitrogen for growth. Thus, one embodiment of the invention may include the use of unadulterated enteric fermentation to not only produce methane-utilizing microorganisms, but to simultaneously reduce feedlot ammonia emissions as well.

In some embodiments, such methods also include using enclosure means and/or methane-consumption means, as detailed above, to reduce dust or suspended particles emissions associated with ruminant animals. In order to increase the efficiency of a methane-driven system as detailed above, a filter may be used to prevent dust and/or other airborne particles from entering into mutual exposure means 119. Thus, a process employed in accordance with the invention may be used to reduce enteric fermentation methane emissions while simultaneously reducing emissions of suspended particles typically associated with ruminant animals.

In some embodiments, such methods further include providing means to convey enclosure air 120 from areas enclosed by enclosure means 115 where enteric fermentation methane is known to accumulate, such as near feeding tracts, roof lines, or other potential methane accumulation areas. Such methods also include situating a means for mutual-exposure containing a methane-consumption means inside of an area enclosed an enclosure means, wherein means may or may not be provided to continuously or mechanically direct enclosure air to contact a methane-consumption system, but in either case causing enteric fermentation to be utilized as a source of energy for the production of methane-based goods.

The above-detailed embodiment pertains to the use of enteric fermentation methane as a novel source of energy for the production of methane-utilizing microorganisms in a confined growth-and-harvest apparatus existing outside of the digestive tract of a ruminant animal. There are a number of potential methods that can be used to carry out a process in accordance with the invention. In particular, there are a number of methods that can be utilized to mutually-expose enteric fermentation methane, methane-utilizing microorganisms, and a microorganism growth-culture medium for the purpose of causing methane-utilizing microorganisms to grow using enteric fermentation methane as a source of carbon and/or energy.

In some embodiments, such methods include confining a ruminant animal to a site provided with means to funnel, convey, and/or direct enteric fermentation methane into an apparatus whereby such enteric fermentation methane is used to grow methane-utilizing microorganisms in a confined apparatus, and whereby the means used to carry out this process are either partially situated on a ruminant animal or not at all situated on a ruminant animal.

In some embodiments, such methods also include providing means to convey enteric fermentation methane from a site where ruminant animals are known to frequent, such as feeding or sleeping areas, to a means for the mutual-exposure of enteric fermentation methane, methane-utilizing microorganisms, and a microorganism growth-culture medium, whereby methane-utilizing microorganisms grow using enteric fermentation methane as a source of carbon and/or energy in an apparatus existing outside of the digestive tract of a ruminant animal.

In some embodiments, such methods also include causing methane-utilizing microorganisms to grow by mutually-exposing enteric fermentation methane, methane-utilizing microorganisms, and a microorganism growth-culture medium in a confined apparatus, wherein some or all of the methane-utilizing microorganisms are genetically-engineered.

In some embodiments, such methods also include growing methane-utilizing microorganisms using enteric fermentation methane as a source of carbon and/or energy for such growth, whereby the means used to carry out the process are powered by solar, wind, methane-based, or other suitable form of power different from the source of power—battery power—mentioned in the above detailed description.

There are also a number of methods in accordance with several embodiments of the invention that can be utilized to mutually-expose enteric fermentation methane, methane-utilizing microorganisms, and a microorganism growth-culture medium for the purpose of causing methane-consumption systems to operate using enteric fermentation methane as a source of carbon and/or energy.

In some embodiments, such methods also include collecting, storing, and/or transporting ruminant animal methane for later use in a process carried out in accordance with the invention.

In any case, the detailed description of one preferred method of carrying out a process in accordance with the invention should serve foremost as an elucidation of the practical and technological feasibility of carrying out the invention, rather than as a limitation of the process of the invention itself.

As described herein, several embodiments of the present invention provide a novel process for the utilization of methane emitted by ruminant animals. Preferred embodiments of the invention provide are particularly advantageous because they:

(i) convert a previously wasted form of energy into a useful end-product, (ii) convert an environmentally-destructive greenhouse gas into a useful end-product, (iii) provide a direct economic incentive for a ruminant animal methane emissions reduction effort, (iv) reduce atmospheric ruminant animal methane emissions without altering the chemical or microbial make-up of the digestive tract of ruminant animals, (v) reduce atmospheric ruminant animal methane emissions without requiring ruminant animals to alter their normal/natural behavior patterns, including sleeping and nutrient-consumption, (vi) reduce atmospheric ruminant animal methane emissions without requiring feed reformulations, selective breeding activities, or chemical or microbial modifications to the digestive systems of ruminant animals, (vii) utilize as a source of energy a material never previously considered a viable source of energy, and/or (viii) have the potential, especially if used widely, to significantly reduce ruminant animal methane emissions.

While the above description of preferred methods of carrying out a process in accordance with embodiments of the invention contains many specificities, these should not be construed as limitations on the scope of the invention. As stated, there are a number of ways to carry out a process in accordance with invention. Accordingly, the scope of the invention should be determined not by the preferred method described, but by the appended claims and their legal equivalents.

What is claimed is:

1. A method for oxidizing methane using a source of oxygen and the enteric fermentation methane produced by one or more ruminant animals as a source of carbon and/or energy, comprising:

a. providing one or more ruminant animals contained in an enclosure;

b. providing a first gas comprising enteric fermentation-derived methane gas that has been emitted by and collected directly from said animals;

c. providing a second gas comprising air that has been combined with said first gas in said enclosure, wherein said second gas comprises oxygen and wherein the concentration of said enteric fermentation-derived methane in said combination of first and second gases is between 1.7 ppm and 1000 ppm;

d. providing a culture of at least one methanotrophic microorganism, wherein said microorganism oxidizes methane to methanol, water, and/or carbon dioxide, wherein said microorganism is unable to utilize said first gas as a sole source of methane;

e. providing a third gas comprising methane, wherein the amount of methane in said third gas is sufficient to support the growth of said at least one microorganism when fed to said microorganism;

f. introducing a combination of said first, second and third gases into a culture chamber comprising said at least one methanotrophic microorganism thereby oxidizing a portion of said methane in both said first and third gases to methanol, water, and/or carbon dioxide.

2. The method of claim 1, wherein an air conveyor is provided to direct, move, and/or convey said second gas, wherein the air conveyor can be used to contact said second gas with said third gas and/or said microorganism.

3. The method of claim 1, wherein said microorganism utilizes methane monooxygenase to oxidize methane to intracellular methanol and/or carbon dioxide, and subsequently utilizes said intracellular methanol and/or carbon dioxide for cellular metabolism.

4. The method of claim 1, wherein said second gas comprises air, dust, non-methane organic matter, ammonia, gases, flies, particulate matter, and/or airborne matter fully or partially contained by said enclosure.

5. The method of claim 1, wherein said second gas is contacted with said microorganism to function as an oxygen source for said microorganism that reduces environmental enteric fermentation methane emissions.

6. The method of claim 1, wherein the flow rate of said second gas conveyed through said enclosure is reduced to increase the concentration of said methane within said enclosure, or wherein the flow rate of said second gas conveyed by said conveyor through said enclosure is increased to reduce the concentration of said methane within said enclosure.

7. The method of claim 1, wherein the temperature and flow rate of said air within said enclosure are simultaneously controlled to optimize the health of said ruminant animals within said enclosure and the concentration of said oxygen and/or methane.

* * * * *

UNITED STATES PATENT AND TRADEMARK OFFICE
CERTIFICATE OF CORRECTION

PATENT NO. : 7,745,197 B1
APPLICATION NO. : 11/208808
DATED : June 29, 2010
INVENTOR(S) : Herrema et al.

It is certified that error appears in the above-identified patent and that said Letters Patent is hereby corrected as shown below:

In column 1 at line 8, Change "6,982,161" to --6,982,161, issued January 3, 2006,--, therefore.

In column 6 at line 61, Change "animals," to --animals;--, therefore.

In column 6 at line 62, Before "to" change "(h)" to --(i)--, therefore.

In column 6 at line 63-64, Change "operations," to --operations;--, therefore.

In column 6 at line 65, Before "to" change "(i)" to --(j)--, therefore.

In column 6 at line 66, Change "utilization" to --utilization;--, therefore.

In column 7 at line 1, Before "to" change "(j)" to --(k)--, therefore.

In column 9 at line 40-41, Change "Brettanomyces petrophilium," to --Brettanomyces petrophilum,--, therefore.

In column 9 at line 65, Change "Bacillus subtilus," to --Bacillus subtilis,--, therefore.

In column 10 at line 21, Change "Archromobacter coagulans," to --Achromobacter coagulans,--, therefore.

Signed and Sealed this
Fifth Day of April, 2011

David J. Kappos
*Director of the United States Patent and Trademark Office*